(12) United States Patent
Rowe et al.

(10) Patent No.: US 11,560,793 B2
(45) Date of Patent: Jan. 24, 2023

(54) GAS ISOTOPE ANALYSIS

(71) Applicant: Halliburton Energy Services, Inc., Houston, TX (US)

(72) Inventors: Mathew Dennis Rowe, Lafayette, LA (US); Jon Troy Gosney, Bellville, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 989 days.

(21) Appl. No.: 16/332,163

(22) PCT Filed: Oct. 13, 2016

(86) PCT No.: PCT/US2016/056848
§ 371 (c)(1),
(2) Date: Mar. 11, 2019

(87) PCT Pub. No.: WO2018/071029
PCT Pub. Date: Apr. 19, 2018

(65) Prior Publication Data
US 2019/0368345 A1  Dec. 5, 2019

(51) Int. Cl.
*E21B 49/00* (2006.01)
*E21B 21/01* (2006.01)
(Continued)

(52) U.S. Cl.
CPC ............ *E21B 49/005* (2013.01); *E21B 21/01* (2013.01); *E21B 49/08* (2013.01); *G01N 30/72* (2013.01);
(Continued)

(58) Field of Classification Search
CPC ........ E21B 49/005; E21B 21/01; E21B 49/08; G01N 30/7206; G01N 30/88;
(Continued)

(56) References Cited

U.S. PATENT DOCUMENTS 7,124,030 B2   10/2006   Ellis et al.
7,174,254 B2   2/2007    Ellis et al.
(Continued)

FOREIGN PATENT DOCUMENTS

EP   1887342   2/2008

OTHER PUBLICATIONS

GB. Application No. GB1901979.3, "First Examination Report", dated Jul. 16, 2021, 4 pages.
(Continued)

*Primary Examiner* — Melissa J Koval
*Assistant Examiner* — Joseph O Nyamogo
(74) *Attorney, Agent, or Firm* — Kilpatrick Townsend & Stockton LLP

(57) ABSTRACT

Systems and methods are provided for analyzing isotopes of a gas from a wellbore to determine geological information associated with the wellbore. A drill device can be used to drill rocks or particles in a wellbore, which can cause a gas to be released within the wellbore. Fluid can be pumped into the wellbore as the drill bit drills the rocks or particles and the fluid, along with the gas released, can flow through the wellbore and to a surface of the wellbore. A gas detector can be positioned near the wellbore for detecting an amount of gas and a type of gas in the fluid and gas mixture and transmitting data about the amount and type of the gas to a computing device. The computing device can output data based on the amount and type of gas in the mixture for determining geological information about the wellbore.

18 Claims, 6 Drawing Sheets

(51) Int. Cl.
*E21B 49/08* (2006.01)
*G01N 30/72* (2006.01)
*G01N 30/88* (2006.01)
*G01N 33/28* (2006.01)
*G01V 5/06* (2006.01)

(52) U.S. Cl.
CPC ......... *G01N 30/7206* (2013.01); *G01N 30/88* (2013.01); *G01N 33/2823* (2013.01); *G01N 2030/8854* (2013.01); *G01N 2030/8868* (2013.01); *G01V 5/06* (2013.01)

(58) Field of Classification Search
CPC ....... G01N 33/2823; G01N 2030/8854; G01N 2030/8868; G01N 30/72; G01V 5/06
See application file for complete search history.

(56) References Cited

U.S. PATENT DOCUMENTS

| | | |
|---|---|---|
| 7,529,626 B1 | 5/2009 | Ellis et al. |
| 8,056,408 B2 * | 11/2011 | Pop ...................... E21B 49/081 73/152.04 |
| 2006/0202122 A1 | 9/2006 | Gunn et al. |
| 2008/0097735 A1 | 4/2008 | Ibrahim et al. |
| 2008/0147326 A1 * | 6/2008 | Ellis ...................... G01V 9/007 702/9 |
| 2013/0233057 A1 | 9/2013 | Karoum et al. |
| 2016/0153955 A1 * | 6/2016 | Strapoc ................ E21B 49/005 702/24 |

OTHER PUBLICATIONS

NZ. Application No. NZ750569, Substantive Examination Report, dated Apr. 23, 2020, 4 pages.

International Patent Application No. PCT/US2016/056848, "International Search Report and Written Opinion", dated Jul. 10, 2017, 16 pages.

* cited by examiner

GAS ISOTOPE ANALYSIS

TECHNICAL FIELD

The present disclosure relates generally to wellbore drilling. More specifically, but not by way of limitation, this disclosure relates to analyzing isotopes of a gas from a wellbore.

BACKGROUND

A well (e.g., oil or gas wells for extracting fluids from a subterranean formation) can include a drilling rig for drilling in a wellbore, along with other components or equipment. During drilling operations, a gas within the wellbore can flow into fluid from the drilling operation, such as drilling fluid or drilling mud. Geological information about the wellbore can be determined based on the gas in the fluid.

DETAILED DESCRIPTION

Figure 1:
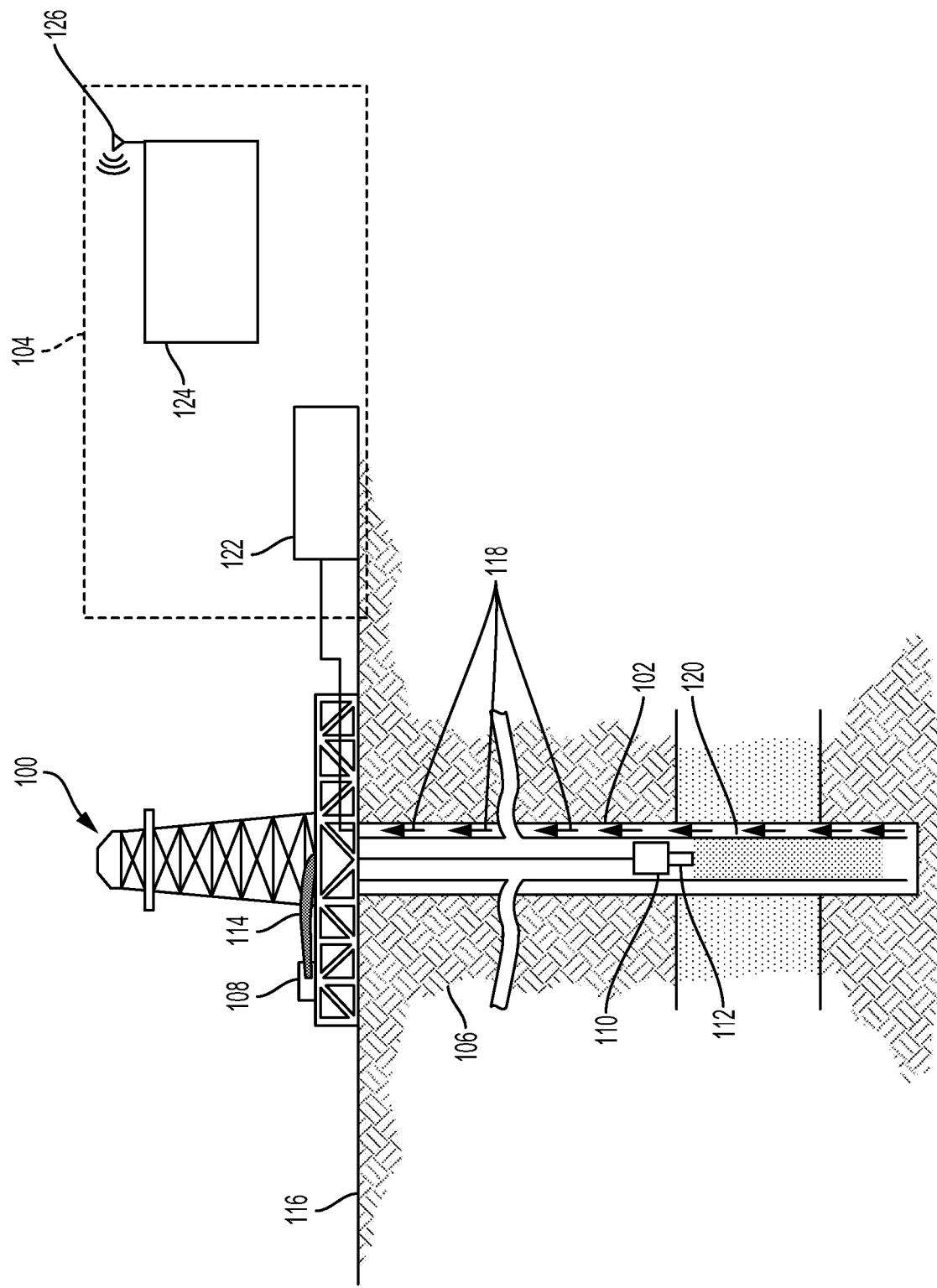
FIG. 1 is a schematic diagram showing a drilling rig on a wellbore, along with a system for analyzing isotopes of a gas from the wellbore to determine geological information about the wellbore according to one example of the present disclosure.

Certain aspects and features of the present disclosure are directed to analyzing isotopes of a gas from a wellbore to determine geological information associated with the wellbore. During drilling operations, a drill bit can be used to cut or penetrate particles or rock in a wellbore and a drilling fluid circulation system or a mud system can circulate fluid, such as drilling fluid or mud, through the wellbore to allow the drill bit to penetrate the rock. As the drill bit penetrates the rock in the wellbore, gas in the wellbore may be released and the gas can flow into the fluid. The fluid, along with the gas, can flow toward a surface of the wellbore. The fluid and gas mixture can be analyzed at the surface of the wellbore to determine isotopic data about the fluid and gas mixture (e.g., to determine an amount of a carbon isotope in the mixture) and the isotopic data can be used to determine geological information about the wellbore.

For example, a depth or location of the drill bit within the wellbore can be tracked and transmitted to a computing device as the drill bit penetrates rock within the wellbore and drilling fluid is pumped through the drill bit. In other examples, the computing device can receive data and determine the depth or location of the drill bit within the wellbore based on the data. The drilling fluid, along with a gas released in the wellbore, can circulate through the wellbore and toward the surface of the wellbore. A gas detector device (e.g., a mass spectrometer) can be positioned at the surface of the wellbore to receive the drilling fluid and gas mixture and detect an amount and a type of gas in the mixture and transmit data about the amount and type of gas to a computing device in real-time (e.g., as the drilling fluid and gas mixture reaches the surface of the wellbore and exits the wellbore). As an example, the gas detector device can detect an amount of one or more isotopes in the mixture (e.g., an amount of a carbon isotope or an amount of a hydrogen isotope in the mixture) using gas chromatography isotope-ratio mass spectrometry and transmit data about the amount of the isotope to the computing device.

The computing device can perform one or more operations based on the isotopic data received from the gas detector device. For example, the computing device can generate a data point based on the isotopic data received from the gas detector device. The data point can indicate a composition of a hydrocarbon in the fluid and gas mixture, along with a depth associated with the mixture (e.g., the depth or location of the drill bit within the wellbore when the drilling fluid was pumped through the drill bit and circulated to the surface of the wellbore) and the computing device can determine geological information about the wellbore based at least in part on the data point. As an example, the computing device can generate a data point associated with a particular location or depth within a wellbore at which drilling fluid is circulated and an amount of a carbon isotope or a hydrogen isotope in a fluid and gas mixture from the particular location or depth. The data point can indicate an amount of ethane or methane at the particular location depth within the wellbore. The computing device can also determine a relationship between the data point and a depth or location within the wellbore. For example, the computing device can apply a regression analysis to the data point and the depth or location within the wellbore associated with the data point to determine a change in the data point based on a change in the depth within the wellbore (e.g., a change in an amount of ethane or methane in the wellbore based on a change in a location or depth within the wellbore). The computing device can then determine geological information about the wellbore or the particular location or depth within the wellbore based on the data point.

In some examples, the gas detector device can analyze fluid and gas mixtures from various depths within the wellbore and transmit data about an amount of an isotope in the mixtures to the computing device. The computing device can generate multiple data points associated with an amount of an isotope in the various mixtures from the various depths within the wellbore. The computing device can then determine geological information about the wellbore based on the various data points and the depths or locations within the wellbore associated with each fluid and gas mixture. As an example, the computing device can determine a boundary of the wellbore (e.g., a shape or physical boundary of the wellbore) based at least in part on the various data points. The computing device can also determine a trend or pattern of isotopic data within the wellbore based at least in part on the various data points.

The computing device can also generate and output data based at least in part on isotopic data received from the gas detector device. The data can indicate an amount of one or more isotopes in a fluid and gas mixture from one or more depths or locations within the wellbore. The data may also indicate an amount of one or more hydrocarbons in a fluid and gas mixture from one or more depths or locations within the wellbore. The data may also indicate a concentration of an amount of gas and a type of gas detected by the gas detector device. In some examples, the computing device can output the data as a chart, plot, graph, etc. for determining geological information about the wellbore. The computing device can generate and output data based at least in part on isotopic data received from the gas detector device as described above and generate and output a visual indicator associated with the data and the visual indicator can be used to determine geological information about the wellbore.

In some examples, the gas detector device and the computing device can be used to determine geological information about a wellbore in real-time (e.g., as a fluid and gas mixture from within the wellbore reaches the surface of the wellbore), which can enhance drilling operations on the wellbore. For example, the gas detector device and the computing device can be used to determine a location of a seal or barrier in the wellbore (e.g., a location of relatively impermeable rock that forms a barrier or cap above and around the wellbore to trap fluids such as, for example, hydrocarbon fluids, such that the fluids cannot migrate), a location of a communication zone in the wellbore (e.g., a location within the wellbore where a fluid can flow from one part of the wellbore to another part of the wellbore or to another wellbore), or gas diffusion at a depth within the wellbore (e.g., movement of molecules of the gas from high concentration to low concentration at the depth within the wellbore). Efficiently determining geological information about the wellbore can lead to effective planning for subsequent drilling operations.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative examples but, like the illustrative examples, should not be used to limit the present disclosure.

FIG. 1 is a schematic diagram showing a drilling rig 100 on a wellbore 102, along with a system 104 for analyzing isotopes of a gas from the wellbore 102 to determine geological information about the wellbore 102 according to one example.

The drilling rig 100 may be used to create a borehole or wellbore 102 that extends through various earth strata (e.g., a hydrocarbon bearing subterranean formation 106). The drilling rig 100 can also include a pump 108, a drill string 110, and a drill bit 112.

The drill string 110 can be coupled to a coiled tubing that can be wound around a reel and deployed into the wellbore 102. In other examples, the drill string 110, along with any components of the drill string 110, can be coupled to a drill pipe and rotated by a top drive or rotary table on the drilling rig 100.

The drill string 110 can include a milling device or the drill bit 112. The drill bit 112 can be any device for cutting or removing particles from within the wellbore 102. During the drilling operations, the pump 108 cam pump a variety of wellbore compositions 114, such as, for example, drilling fluid or drilling mud, through the drill string 110. Pumping drilling fluid through the drill string 110 may allow the drill bit 112 to drill or cut through the formation 106. The drill string 110 can transmit the drilling fluid to the drill bit 112 and the drilling fluid can exit into the wellbore 102 through the drill bit 112.

In the example depicted in FIG. 1, the wellbore 102 has been drilled from a surface 116 and through subterranean formation 106. As the wellbore 102 is drilled, the drill bit 112 can cut into rocks or sediments in the wellbore 102, which can allow a gas within the wellbore (e.g., a gas within the formation 106) to be released. While the drill bit 112 cuts into the wellbore 102, drilling fluid is pumped through drill bit 112 and into the wellbore 102, which can enhance drilling operations and allow the gas released in the wellbore 102 to flow into the drilling fluid. The fluid and gas mixture can flow along a flow path 118 as the drilling fluid circulates back to the surface 116 via a wellbore annulus 120. At the surface 116, the fluid and gas mixture can be analyzed or processed. For example, the system 104 can be used to analyze isotopes in the fluid and gas mixture to determine geological information about the wellbore 102.

The system 104 can include a gas detector 122, which can be used to analyze a fluid and gas mixture from a wellbore. The gas detector 122 can be any type of device operable in a well system for analyzing a fluid and gas mixture to determine isotopic data about the gas in the mixture (e.g., determining an amount of an isotope in the mixture). The gas detector 122 can be positioned proximate to the surface 116 to receive the fluid and gas mixture as the mixture reaches the surface 116 and analyze the mixture to determine isotopic data about the gas in the mixture. For example, the gas detector 122 can detect an amount and a type of a gas or an amount and a type of a gas isotope in the mixture. As an example, the gas detector 122 can analyze the mixture to detect a presence and an amount of a carbon isotope or a hydrogen isotope in the fluid and gas mixture. As another example, the gas detector 122 can detect a concentration level of an amount of gas and a type of gas in the fluid and gas mixture. The gas detector 122 can also analyze the composition 114 entering the wellbore 102 and detect a type of a gas or isotope or an amount of the gas or isotope in the composition 114 entering the wellbore 102. Positioning the gas detector 122 proximate to the wellbore 102 or proximate to the surface 116 can allow the gas detector 122 to efficiently analyze and obtain isotopic data about a gas in fluid entering or exiting the wellbore 102. In some examples, positioning the gas detector 122 proximate to the surface 116 or proximate to the wellbore 102 can also allow the gas detector 122 to determine isotopic data about a gas in a fluid entering or exiting the wellbore 102 in real-time (e.g., as the fluid and gas mixture enters the wellbore 102 or as the fluid and gas mixture reaches the surface 116).

In some examples, the gas detector 122 may not be included in the well system. In such examples, a sample of a drilling fluid and gas mixture can be collected from the wellbore 102, including without limitation, through manual collection (e.g., manual labor) or through automated collection (e.g., by an apparatus, device, machine, or the like). The sample may be transported to a location (e.g., to an onsite or offsite laboratory) for analyzing the sample to determine isotopic data about the gas in the mixture.

The system 104 can also include a computing device or processing module 124. The computing device 124 can be positioned at the surface 116 or offsite. The computing device 124 can include a communication device 126 for transmitting and receiving data. The communication device 126 can represent one or more of any components that facilitate a network connection and the computing device 124 can be communicatively coupled to the gas detector 122 via the communication device 126. The computing device 124 can also transmit data to a remote location (e.g., to an offsite laboratory or to another computing device) or receive data from the remote location via the communication device 126.

The computing device 124 can be used to generate data based on data received from the gas detector 122. For example, the computing device 124 can generate one or more data points based on isotopic data about a fluid and gas mixture received from the gas detector 122. The data points can indicate a composition of a hydrocarbon in the fluid and gas mixture, along with a depth associated with the mixture (e.g., a depth or location of the drill bit 112 within the wellbore 102 when the drilling fluid was pumped through the drill bit 112 and circulated to the surface 116). The computing device 124 can also determine geological information about the wellbore 102 based at least in part on the one or more data points or isotopic data received from the gas detector 122. As an example, the computing device 124 can determine a boundary of the wellbore (e.g., a shape or physical boundary of the wellbore) based at least in part on the one or more data points or isotopic data received from the gas detector 122. The computing device 124 can also generate and output a visual indicator associated with geological information about the wellbore 102 determined by the computing device 124. For example, the computing device 124 can determine a boundary of the wellbore 102 based on isotopic data received from the gas detector 122 and generate and output a visual indicator associated with the boundary (e.g., a color coded indicator corresponding to the boundary of the wellbore 102).

The computing device can also determine isotopic data trends or patterns within the wellbore (e.g., a trend or pattern of a presence or amount of a gas in the wellbore) based at least in part on the one or more data points or isotopic data received from the gas detector 122.

In some examples, the computing device 124 can output data for determining geological information about the wellbore 102. For example, the computing device 124 can output isotopic data received from the gas detector 122 (e.g., data about an amount of a carbon isotope in a mixture from the wellbore 102) for determining geological information about the wellbore 102. The computing device 124 can also output one or more data points generated by the computing device 124 based on data received from the gas detector 122 for determining geological information about the wellbore 102. For example, the computing device 124 can output one or more of a graph, plot, chart, etc. that includes one or more data points generated by the computing device 124 or isotopic data received from the gas detector 122 and the data output by the computing device 124 can be used to determine geological information about the wellbore 102. As an example, the data can be used to determine a boundary of the wellbore 102, a location of a seal or barrier in the wellbore 102 (e.g., a location of relatively impermeable rock that forms a barrier or cap above and around the wellbore 102 to trap fluids such as, for example, hydrocarbon fluids, such that the fluids cannot migrate), a location of a communication zone in the wellbore 102 (e.g., a location within the wellbore 102 where a fluid can flow from one part of the wellbore to another part of the wellbore 102 or to another wellbore), or gas diffusion at a depth within the wellbore 102 (e.g., movement of molecules of the gas from high concentration to low concentration at the depth within the wellbore 102).

The computing device 124 can also generate and output data based on isotopic data received from the gas detector 122 and generate and output a visual indicator associated with the data. As an example, the computing device 124 can generate and output a color coded graph, plot, chart, etc. that includes one or more data points generated by the computing device 124 based on isotopic data received from the gas detector 122. The visual indicator generated by the computing device 124 can be used to determine geological information about the wellbore 102.

In some examples, determining geological information about the wellbore 102 or generating and outputting data for determining geological information about the wellbore 102 can enhance drilling operations on the wellbore 102 and can lead to effective planning for subsequent drilling operations.

Figure 2:
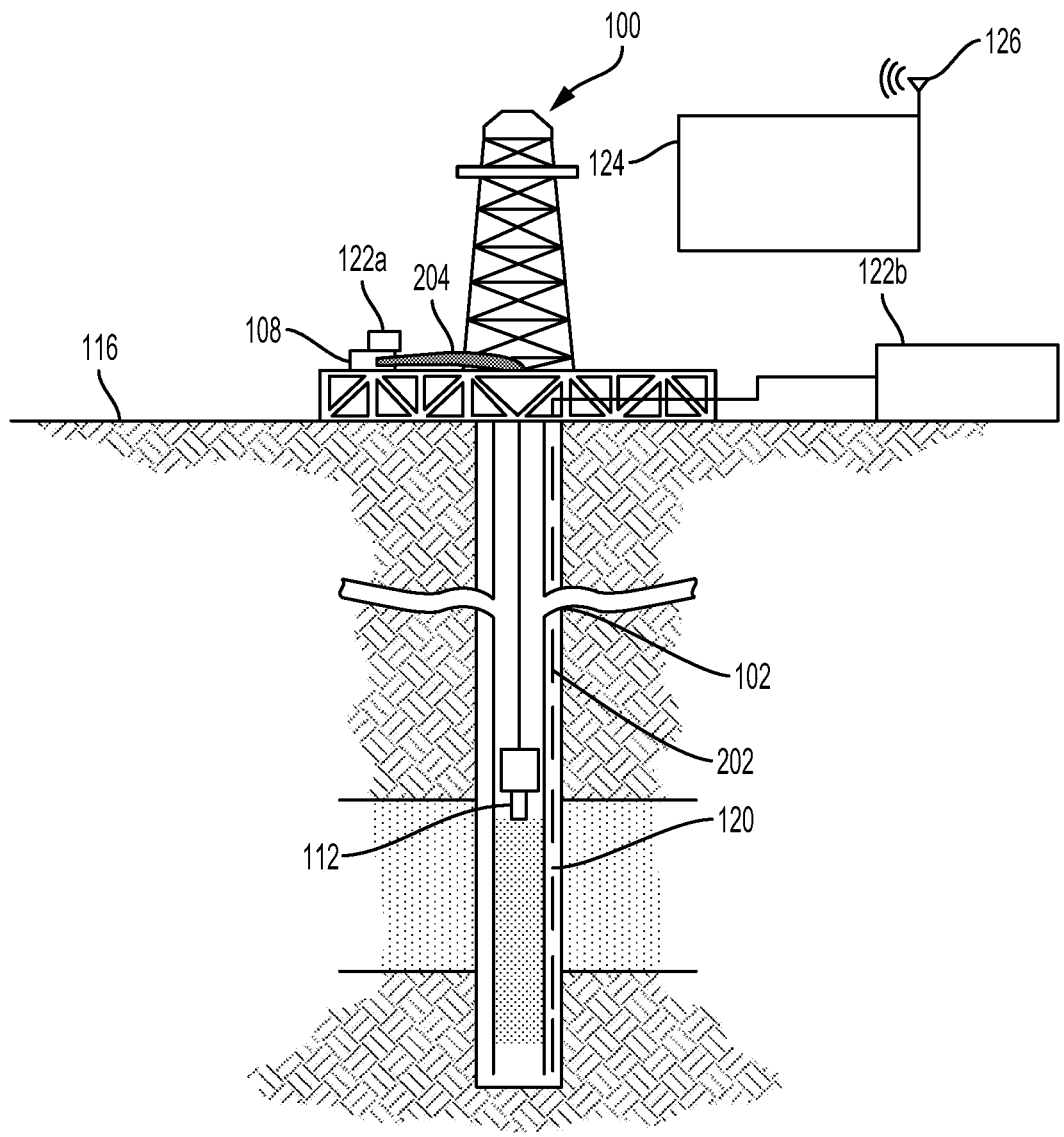
FIG. 2 is a schematic diagram of the drilling rig of FIG. 1, along with a fluid and gas mixture traveling from within the wellbore to the surface of the wellbore according to one example of the present disclosure.

In some examples, the gas detector 122, along with the computing device 124 can be used to analyze isotopes of a gas in a fluid and gas mixture entering or exiting the wellbore 102 to determine geological information about the wellbore 102. FIG. 2 is a schematic diagram of the drilling rig 100 of FIG. 1, along with a fluid and gas mixture 202 traveling from within the wellbore 102 to the surface 116 of the wellbore 102.

In the example depicted in FIG. 2, a fluid flow stream 204 is being pumped into the wellbore 102 by the pump 108 through the drill string 110. The fluid flow stream 204 can include drilling fluid or drilling mud and drilling fluid gas (e.g., a gas included in the drilling fluid or drilling mud being pumped through the drill string 110 by the pump 108). A drill bit 112 can penetrate rocks within the wellbore 102 and gas from within the wellbore 102 (e.g., gas within the formation 106) can be released as the drill bit 112 penetrates the rocks. The gas can flow into drilling fluid pumped into the wellbore 102 through the drill bit 112 and a fluid and gas mixture 202 can flow to the surface 116 of the wellbore 102 via the wellbore annulus 120.

In some examples, more than one gas detector may be used to analyze a fluid and gas mixture entering or exiting the wellbore 102 to obtain isotopic data about the fluid and gas mixtures in the well system depicted In FIG. 2. For example, gas detectors 122*a-b* can be used to analyze the fluid flow stream 204 and the fluid and gas mixture 202. The gas detectors 122*a-b* can be of the same type or can be different and can each be positioned at the surface 116 of the wellbore 102 or elsewhere in the well system for analyzing the fluid flow stream 204 and the fluid and gas mixture 202.

For example, the gas detector 122*a* can be positioned near the surface 116 and fluid flow stream 204. The gas detector 122*a* can be positioned between the wellbore 102 and the fluid flow stream 204 to analyze the fluid flow stream 204 prior to the fluid flow stream 204 entering the wellbore 102. In this manner, the gas detector 122*a* can be used to determine isotopic data about a gas in the fluid flow stream 204 (e.g., drilling fluid gas in the fluid flow stream 204) as the fluid flow stream 204 is pumped into the wellbore 102. As an example, the gas detector 122*a* can be used to detect an amount of a carbon isotope or an amount of a hydrogen isotope in the fluid flow stream 204 as the fluid flow stream 204 is pumped into the wellbore 102. As another example, the gas detector 122*a* can detect a concentration of a carbon isotope or a hydrogen isotope in the fluid flow stream 204 as the fluid flow stream 204 is pumped into the wellbore 102.

The gas detector 122*b* can be positioned near the surface 116 and the fluid and gas mixture 202. The gas detector 122*b* can be used to analyze the fluid and gas mixture 202 exiting the wellbore 102 to determine isotopic data about a gas in the fluid and gas mixture 202 as the fluid and gas mixture 202 exits the wellbore 102. For example, the gas detector 122*b* can be used to determine an amount or concentration of a carbon isotope or an amount of a hydrogen isotope in the fluid and gas mixture 202 as the fluid and gas mixture 202 reaches the surface 116 and exits the wellbore 102.

In some examples, a known type or amount of a gas may be included in the fluid flow stream 204 entering the wellbore 102. In other examples, an unknown type or amount of gas is included in the fluid flow stream 204. The gas detector 122*a* can determine isotopic data about the gas in the fluid flow stream 204 entering the wellbore and transmit the isotopic data to a computing device 124 via communication device 126. The gas detector 122*b* can determine isotopic data about the gas in the fluid and gas mixture 202 as the fluid and gas mixture 202 exits the wellbore 102 and transmit the isotopic data to the computing device 124 via the communication device 126. The computing device 124 can generate one or more data points based on data received from the gas detectors 122*a-b* as described above with regard to FIG. 1. The computing device 124 can also determine geological information about the wellbore 102 or output data for determining geological information about the wellbore 102 based at least in part on data received from the gas detectors 122*a-b* in substantially the same manner as described above with regard to FIG. 1. In some examples, the computing device 124 can receive isotopic data about a gas in the fluid flow stream 204 from the gas detector 122*a* and receive isotopic data about a gas in the fluid and gas mixture 202 from the gas detector 122*b*. The computing device 124 can compare the isotopic data received from the gas detectors 122*a-b* to determine a ratio between an amount of a gas or isotope of a gas entering the wellbore 102 and an amount of a gas or isotope of a gas exiting the wellbore 102.

In some examples, one or more of the gas detectors 122*a-b* shown in FIG. 2 can be positioned such that the gas detector 122*a-b* is partially within or fully within the wellbore 102. For example, the gas detector 122*a* can be positioned on an outer housing of the drill bit 112. In other examples, the gas detector 122*a* can be positioned within the outer housing of the drill bit 112. In such examples, the gas detector 122*a* can transmit data (e.g., to the computing device 124) via a wired drill pipe, a wired coil tubing, or by using other telemetry schemes (e.g., acoustic telemetry, electromagnetic telemetry, mud pulse telemetry, or any combination thereof) if the gas detector 122*a* is positioned partially within or fully within the wellbore 102. Positioning the gas detector 122*a* partially or fully within the wellbore 102 can allow the gas detector 122*a* to more accurately and efficiently analyze the fluid flow stream 204 as the fluid flow stream 204 enters the wellbore 102, which can allow a more accurate analysis of gas released in the wellbore 102 for determining geological information about the wellbore 102.

In still another example, any of the gas detectors 122*a-b* and a computing device 124 can be integrated into a single structure. For example, a gas detector 122*b* and the computing device 124 can be within a single housing. The computing device 124 can be communicatively coupled to a display device for outputting data. The computing device 124 can also include a communication device 126 for transmitting and receiving data. The computing device 124 may transmit data to a remote location (e.g., to a drilling or well operator or another computing device).

Although a single wellbore 102 is shown in FIG. 1-2, in some examples, a gas detector and a computing device can be used to analyze isotopes of a gas from multiple wellbores to determine geological information about the various wellbores.

Figure 3:
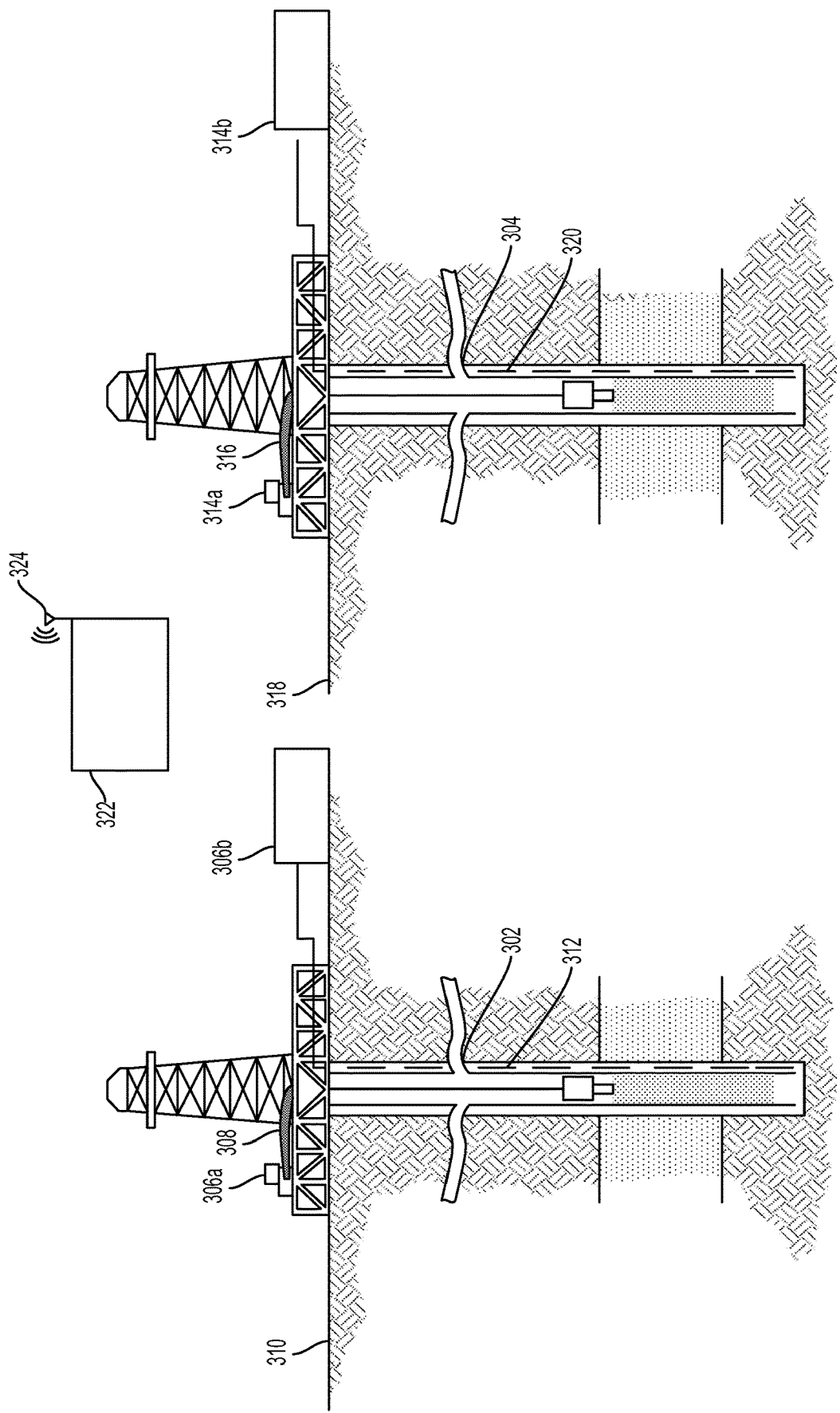
FIG. 3 is a schematic diagram of multiple wellbores, along with a system for analyzing isotopes of a gas from each wellbore to determine geological information about the wellbore according to one example of the present disclosure.

For example, FIG. 3 is a schematic diagram of multiple wellbores 302, 304, along with a system for analyzing isotopes of a gas from each wellbore to determine geological information about the wellbore according to one example of the present disclosure.

In the example depicted in FIG. 3, gas detectors 306*a-b* and 314*a-b* can be positioned near wellbores 302, 304. Each of the gas detectors 306*a-b* and 314*a-b* can be configured in substantially the same manner as gas detector 122 of FIG. 1 and can be used to analyze various fluid and gas mixtures entering or exiting the wellbores 302, 304.

For example, the gas detector 306*a* can analyze a fluid flow stream 308 prior to the fluid flow stream 308 entering the wellbore 302 to determine isotopic data about a gas in the fluid flow stream 308. The gas detector 306*b* can be positioned near a surface 310 of the wellbore 302 and can be used to analyze a fluid and gas mixture 312 exiting the wellbore 302 to determine isotopic data about a gas in the fluid and gas mixture 312 as the fluid and gas mixture 312 exits the wellbore 302. Gas detector 314*a* can analyze a fluid flow stream 316 prior to the fluid flow stream 316 entering the wellbore 304 to determine isotopic data about a gas in the fluid flow stream 316. The gas detector 314*b* can be positioned near a surface 318 of the wellbore 304 and can analyze a fluid and gas mixture 320 exiting the wellbore 304 to determine isotopic data about a gas in the fluid and gas mixture 320 as the fluid and gas mixture 320 exits the wellbore 304.

The gas detector 306*a-b*, 314*a-b* can transmit data about a gas detected in fluid flow streams 308, 316 or a gas detected in fluid and gas mixtures 312, 320 to one or more computing devices 322 via communication device 324. The computing device 322 and the communication device 324 can be respectively configured in substantially the same manner as the computing device 124 and the communication device 126 of FIG. 1. The computing device 322 can generate one or more isotopic data points, determine geological information about one or more of the wellbores 302, 304, or output data for determining geological information about one or more of the wellbores 302, 304 based on data received from the gas detectors 306*a-b*, 314*a-b* in substantially the same manner as described above with regard to FIG. 1-2.

Figure 4:
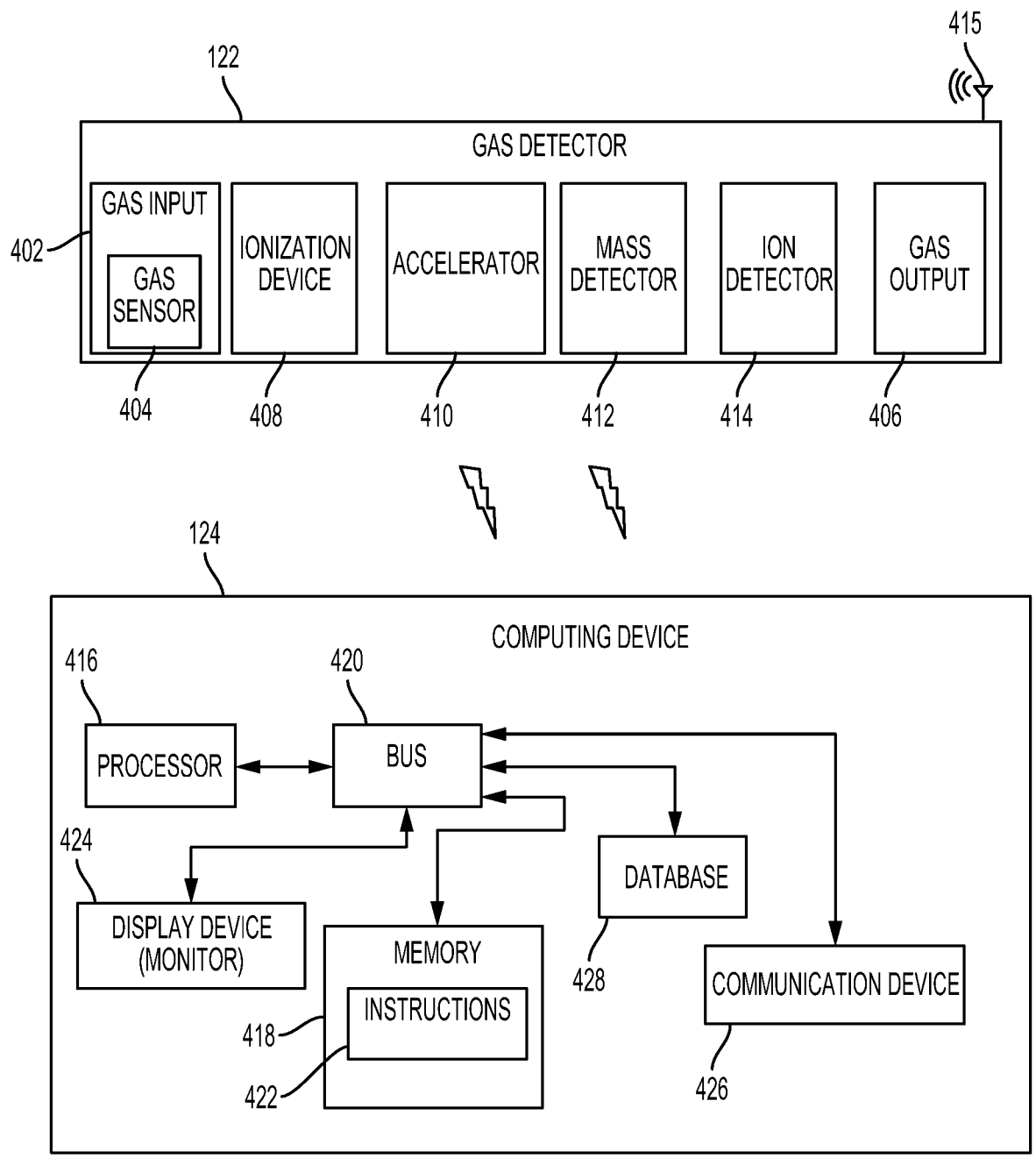
FIG. 4 is a block diagram of an example of a gas detector of FIG. 1, along with a computing device of FIG. 1 for analyzing isotopes of a gas from a wellbore to determine geological information about the wellbore according to one example of the present disclosure.

FIG. 4 is a block diagram of an example of a gas detector 122, along with a computing device 124 for analyzing isotopes of a gas from a wellbore to determine geological information about the wellbore.

The gas detector 122 can be any type of device operable in a well system for measuring an amount of gas or detecting a type of gas. For example, the gas detector 122 can include a mass spectrometer, a cavity ring-down spectrometer, an electromechanical gas detector, a catalytic gas detector, or an infrared gas detector for detecting a gas or an isotope of a gas or a type of gas or an isotope of a gas in a fluid and gas mixture. In some examples, the gas detector 122 can measure an amount of gas or detect a type of gas in a fluid and gas mixture using various techniques, including for example, gas chromatography isotope-ratio mass spectrometry.

The gas detector 122 can include a gas input 402, a gas sensor 404, and gas output 406. The gas input 402 can allow a fluid and gas mixture (e.g., the fluid and gas mixture 202 or the fluid flow stream 204 of FIG. 2) to flow into the gas detector 122 and the mixture can exit the gas detector 122 via the gas output 406. For example, a fluid and gas mixture can flow from within a wellbore (e.g., the wellbore 102) to a surface of the wellbore (e.g., the surface 116), into the gas input 402, and through the gas output 406. In another example, a pump (e.g., the pump 108 of FIG. 1) can pump a fluid and gas mixture and the mixture can flow into the gas input 402, through the gas detector 122, through the gas output 406, and into the wellbore (e.g., via the drill bit 112 of FIG. 1). The gas sensor 404 can detect a presence of an amount of a gas and a type of gas in a fluid and gas mixture prior to the mixture entering the gas detector 122 and the mixture can flow out of the gas detector 122 after the amount of the gas in the mixture is measured by the gas detector 122 or after the type of gas in the mixture is detected by the gas detector 122.

The gas detector 122 can detect an amount of gas and a type of gas in a fluid and gas mixture using various methods and techniques. For example, the gas detector 122 can detect an amount and a type of a gas isotope in a fluid and gas mixture by measuring a mass-to-charge ratio of molecules in the fluid and gas mixture. As an example, the gas detector 122 can detect an amount of a carbon isotope (e.g., carbon-12, carbon-13, or any other carbon isotope) or an amount of a hydrogen isotope in the fluid and gas mixture.

The gas detector 122 can also detect an amount of gas and a type of gas entering a wellbore and an amount of gas and a type of gas exiting the wellbore. The gas detector 122 can also be communicatively coupled to a computing device (e.g., the computing device 124) via a wired or a wireless link. The gas detector 122 can transmit data about an amount and type of a gas in a fluid and gas mixture to the computing device.

In some examples, the gas detector 122 can include one or more additional components for detecting an amount of gas and a type of gas in a fluid and gas mixture. In the example depicted in FIG. 4, the gas detector 122 can also include an ionization device 408, an accelerator 410, a mass detector 412, and an ion detector 414. In such examples, the gas detector 122 can be a mass spectrometer.

The ionization device 408 can be any device for converting a chemical compound into ions. The ionization device 408 can convert a chemical compound into ions by any ionization method, including, for example, protonation, cationization, deprotonation, etc. In some examples, a fluid and gas mixture entering or exiting a wellbore (e.g., the fluid and gas mixture 202 or the fluid flow stream 204 of FIG. 2) can flow into the gas detector 122 via the gas input 402 and the ionization device 408 can convert gas in the mixture into ions as the mixture enters the gas detector 122.

The accelerator 410 can be any device for propelling or accelerating ions. In some examples, the accelerator 410 can be coupled to the ionization device 408 and the accelerator 410 may propel ions from the ionization device 408 to the mass detector 412 using electric charges or fields.

The mass detector 412 can analyze ions produced by the ionization device 408. In some examples, the mass detector 412 can analyze ions by separating ions. The mass detector 412 can separate ions based on a mass to charge ratio of each ion. For example, the mass detector 412 can generate an electric or magnetic field within the gas detector 122. The mass detector 412 can also vary a strength of the electric or magnetic field. The electric or magnetic field can deflect ions propelled into the mass detector 412 by the accelerator 410. The amount of deflection of each ion can vary based on the mass of the ion and the charge of the ion. For example, an ion with a lower mass can be deflected more than an ion with a higher mass. As another example, an ion with a more positive charge can be deflected more than an ion with a less positive charge. In this manner, the mass detector 412 can separate the ions based on a mass to charge ratio of each ion.

The ion detector 414 can be any device for detecting charged particles (e.g., an electron multiplier). In some examples, the mass detector 412 can be coupled to the ion detector 414 and the mass detector 412 can discharge ions into the ion detector 414 based on the mass to charge ratio of each ion. The ion detector 414 can detect each ion as the ions flow through the ion detector 414. For example, the ion detector 414 can detect each ion based on a current generated as the ion travels through the ion detector 414. The gas detector 122 can transmit data about each ion to a computing device (e.g., the computing device 124) as the ion detector 414 detects each ion. In some examples, the gas detector 122 can transmit data about an amount of an ion detected by the ion detector 414 or a type of an ion detected by the ion detector 414 to the computing device for determining an amount of a gas or a type of a gas detected by the gas detector 122.

The gas detector 122 can transmit and receive data from the computing device 124 via a communication device 415. In some examples, the communication device 415 can represent one or more components that facilitate a network connection. In some examples, the communication device 415 may be wireless and can include wireless interfaces such as IEEE 802.11, Bluetooth, or radio interfaces for accessing cellular telephone networks (e.g., transceiver/antenna for accessing a CDMA, GSM, UMTS, or other mobile communications network). In another example, the communication device 415 can be wired and can include interfaces such as Ethernet, USB, IEEE 1394, or a fiber optic interface.

The computing device 124 can be used to determine geological information about a wellbore (e.g., the wellbore 102 of FIG. 1) or to generate and output data for determining geological information about the wellbore based at least in part on data received from the gas detector 122.

The computing device 124 can include a processor 416, a memory 418, and a bus 420. The processor 416 can execute one or more operations for operating the computing device 124. The processor 416 can execute instructions 422 stored in the memory 418 to perform the operations. Non-limiting examples of the processor 416 include a Field-Programmable Gate Array ("FPGA"), an application-specific integrated circuit ("ASIC"), a microprocessor, etc.

The processor 416 can be communicatively coupled to the memory 418 via the bus 420. The memory 418 may include any type of memory device that retains stored information when powered off. Non-limiting examples of the memory 418 include electrically erasable and programmable read-only memory ("EEPROM"), flash memory, or any other type of non-volatile memory. In some examples, at least some of the memory 418 can include a computer-readable medium from which the processor 416 can read the instructions 422. The computer-readable medium can include electronic, optical, magnetic, or other storage devices capable of providing the processor 416 with computer-readable instructions or other program code. Non-limiting examples of a computer readable-medium include (but are not limited to) magnetic disk(s), memory chip(s), ROM, random-access memory ("RAM"), an ASIC, a configured processor, optical storage, or any other medium from which a computer processor can read instructions. The instructions can include processor-specific instructions generated by a compiler or an interpreter from code written in any suitable computer-programming language, including, for example, C, C++, C#, etc.

In some examples, the computing device 124 can include input/output interface components (e.g., a display device 424 and a communication device 426). The computing device 124 can also include other input/output interface components such as a keyboard, touch-sensitive surface, mouse, and additional storage.

The computing device 124 can receive data from a gas detector (e.g., the gas detector 122) via the communication device 426. The computing device 124 can also receive data from a remote location via the communication device 426. In some examples, the communication device 426 can represent one or more of any components that facilitate a network connection. In some examples, the communication device 426 may be wireless and can include wireless interfaces such as IEEE 802.11, Bluetooth, or radio interfaces for accessing cellular telephone networks (e.g., transceiver/antenna for accessing a CDMA, GSM, UMTS, or other mobile communications network). In another example, the communication device 426 can be wired and can include interfaces such as Ethernet, USB, IEEE 1394, a landline, or a fiber optic interface.

The processor 416 can include one processing device or multiple processing devices. The processor 416 can execute one or more operations for determining geological information about a wellbore. For example, the instructions 422 can cause the processor 416 to execute one or more operations for determining geological information about a wellbore based at least in part on data transmitted from a gas detector device (e.g., the gas detector 122) to the computing device 124. In another example, the processor 416 can execute one or more operations for generating and outputting data for determining geological information about the wellbore based on data transmitted from the gas detector device.

In some examples, the processor 416 can execute one or more operations for causing the computing device 124 to transmit data to a remote location (e.g., an offsite laboratory) for determining geological information about the wellbore. In some examples, the data may be analyzed at the remote location (e.g., by an operator or by another computing device) for determining geological information about the wellbore. The processor 416 may execute one or more operations for causing the computing device 124 to receive other data from the remote location. The other data may represent geological information about the wellbore or any other data about the wellbore.

In some examples, the computing device 124 can also be communicatively coupled to the display device 424 via the bus 420. The display device 424 can display data that may correspond to data received by the computing device 124 from the gas detector 122 (e.g., isotopic data indicating an amount and type of an isotope of a gas in a fluid and gas mixture entering or exiting the wellbore 102 of FIG. 1-2). The display device 424 may also display data that may correspond to data generated by executing an operation executed by the processor 416.

The computing device 124 can also be communicatively coupled to a database 428 via the bus 420. The database 428 can store data that may correspond to data received by the computing device 124 from the gas detector 122. The database 428 may also store data that may correspond to data generated by an operation executed by the processor 416. In still another example, the database 428 may store data that may correspond to data received by the computing device 124 from a remote location (e.g., from a computing device positioned at the remote location) or indicia of user input (e.g., if a user programs the computing device 124 to include data).

Figure 5:
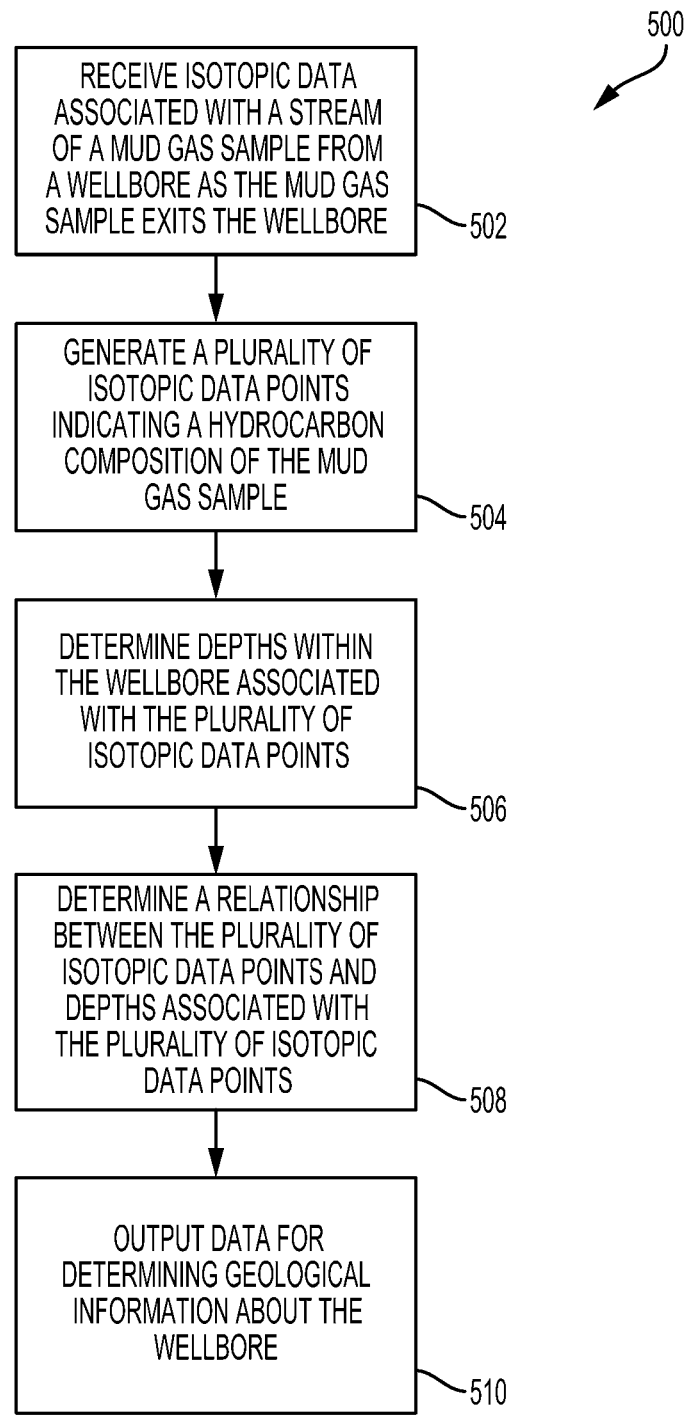
FIG. 5 is a flow chart depicting an example of a process for analyzing isotopes of a gas from a wellbore to determine geological information about the wellbore according to one example of the present disclosure.

FIG. 5 is a flow chart depicting an example of a process 500 for analyzing isotopes of a gas from a wellbore to determine geological information about the wellbore.

In block 502, isotopic data associated with a stream of a mud gas sample from a wellbore is received as the mud gas sample exits the wellbore. In some examples, the mud gas sample includes a mixture of a fluid and a gas from the wellbore and a computing device (e.g., the computing device 124) can receive the isotopic data associated with the stream of the mud gas sample from a gas detector (e.g., the gas detector 122).

For example, a well system can include a pump (e.g., the pump 108 of FIG. 1) and a drill bit (e.g., the drill bit 112). The pump can pump a fluid, such as, for example, drilling fluid or drilling mud, through the drill bit as the drill bit cuts into rocks or particles in the wellbore. As the drill bit cuts into rocks or particles in the wellbore, a gas (e.g., carbon, hydrogen, or a carbon or hydrogen isotope) within the wellbore can be released within the wellbore. Pumping the fluid into the wellbore as the drill bit cuts into the rocks can allow the gas released in the wellbore to flow into the fluid being pumped into the wellbore and form a fluid and gas mixture and the mixture can flow along a path toward a surface of the wellbore.

A gas detector can be positioned at or near the surface of the wellbore to receive the mud gas sample and analyze the sample to determine the isotopic data associated with the sample. In another example, the gas detector can be positioned at a remote location (e.g., an offsite laboratory) to receive the mud gas sample and analyze the sample to determine isotopic data associated with the sample. The gas detector can include a mass spectrometer, a cavity ringdown spectrometer, an electromechanical gas detector, a catalytic gas detector, or an infrared gas detector for detecting an amount or concentration of a gas in the mud gas sample and a type of the gas in the sample. As an example, the gas detector can be a magnetic sector mass spectrometer for detecting an amount of carbon, hydrogen, a carbon isotope, or a hydrogen isotope in the mud gas sample. The gas detector can also measure an amount of gas or detect a type of gas in the mud gas sample using various techniques, including for example, gas chromatography isotope-ratio mass spectrometry. The gas detector may also detect a concentration level of the amount of gas and the type of gas in the mud gas sample.

The gas detector can transmit isotopic data to the computing device and the isotopic data can indicate an amount of gas and a type of gas detected in the mud gas sample. The gas detector may transmit other data that represents a concentration level of the amount of gas and the type of gas detected in the mud gas sample. The data may also represent an amount of gas and a type of gas entering the wellbore and an amount of gas and a type of gas exiting the wellbore.

In block 504, various isotopic data points indicating a hydrocarbon composition of the mud gas sample is generated. In some examples, the computing device can generate the various isotopic data points. For example, the computing device can generate the various isotopic data points based at least in part on data received from a gas detector (e.g., isotopic data transmitted from the gas detector to the computing device in block 502).

For example, the computing device can receive data indicating an amount or a concentration level of a gas and a type of gas detected by the gas detector in a mud gas sample at a surface of the wellbore as the sample exits the wellbore. The computing device can execute operations for generating an isotopic data point based at least in part on the amount or concentration level of the gas and the type of gas detected by the gas detector. As an example, the computing device can receive data from the gas detector indicating an amount or concentration level of a carbon isotope or a hydrogen isotope in a mud gas sample from within a wellbore. The computing device can generate a data point associated with the amount or concentration level of the hydrogen isotope or carbon isotope in the mud gas sample from within the wellbore. The computing device can also execute operations for generating various isotopic data points and each isotopic data point can be associated with an amount and type of a gas in a mud gas sample from within the wellbore.

In some examples, in block 504, the computing device can execute operations for comparing an amount and type of a first gas in a mud gas sample from within the wellbore and an amount and type of a second gas in the mud gas sample. The computing device can also execute operations for comparing an amount and type of a first isotope in a mud gas sample from within the wellbore and an amount and type of a second isotope in the mud gas sample. In some examples, the computing device can generate an isotopic data point indicating a comparison between an amount and type of a first gas or first isotope in a mud gas sample and an amount and type of a second gas or second isotope in the mud gas sample.

For example, the gas detector can transmit data indicating an amount of carbon-12 in a mud gas sample and data indicating an amount of carbon-13 in the mud gas sample. The computing device can compare the amount of carbon-12 and the amount of carbon-13 to determine a ratio between the amount of carbon-12 and the amount of carbon-13 in the mud gas sample and generate an isotopic data point indicating the ratio. As another example, the computing device can compare an amount of C2 to an amount of C1 to determine a ratio between the amount of C2 and the amount of C1 and generate an isotopic data point indicating the ratio. In another example, the computing device can compare an amount of C3 to an amount of C1 to determine a ratio between the amount of C3 and the amount of C1 and generate an isotopic data point indicating the ratio. In still another example, the computing device can compare an amount of C4 to an amount of C1 to determine a ratio between the amount of C4 and the amount of C1 and generate an isotopic data point indicating the ratio.

In block 506, depths within the wellbore associated with the various isotopic data points are determined. In some examples, the computing device can determine the depths within the wellbore associated with the various isotopic data points.

For example, the computing device can determine a depth associated with an isotopic data point based on data received by the computing device. As an example, a depth or location of the drill bit within a wellbore can be tracked and the computing device can receive data indicating a depth or location of the drill bit within the wellbore (e.g., from another computing device) or indicia of a user input (e.g., if the user programs the computing device to include the data). The depth of the drill bit within the wellbore can correspond to a depth or location within the wellbore where drilling fluid or drilling mud was pumped through the drill bit and circulated to the surface of the wellbore.

In other examples, the computing device can determine the depth or location of the drill bit within the wellbore at which fluid is pumped to determine a depth associated with an isotopic data point based on other data. For example, the computing device can receive other data that includes a volume of an annulus of the wellbore, a speed or velocity of a fluid being pumped into the wellbore, a time that the fluid is pumped into the wellbore, and a time that the fluid returns to a surface of the wellbore. The computing device can compare the volume of the annulus of the wellbore, the velocity of the fluid pumped into the wellbore, the time that the fluid is pumped into the wellbore, and the time that the fluid returns to the surface of the wellbore to determine the location or depth of the drill bit within the wellbore.

The computing device can correlate a depth or location within a wellbore at which fluid is pumped into the wellbore and isotopic data from a mud gas sample from the depth within the wellbore to determine depths associated with one or more isotopic data points generated by the computing device (e.g., in block 504).

In block 508, a relationship between the various isotopic data points and depths within the wellbore associated with the various isotopic data points is determined. In some examples, the computing device can determine the relationship between the isotopic data points and depths within the wellbore associated with the isotopic data points.

For example, the computing device can execute operations for using various methods or techniques to determine the relationship between the various isotopic data points and depths within the wellbore associated with the isotopic data points. As an example, the computing device can determine the relationship between the various isotopic data points and depths within the wellbore associated with the isotopic data points by applying a regression analysis to the various isotopic data points and depths within the wellbore associated with the isotopic data points. Regression analysis may include determining a change in one or more of the isotopic data points based on a change in the depth within the wellbore.

In block 510, data is output for determining geological information about the wellbore. In some examples, the computing device can output the data for determining geological information about the wellbore. The geological information about the wellbore can include a boundary of the wellbore, a location of a seal or barrier in the wellbore, a location of a communication zone in the wellbore, or gas diffusion at a depth within the wellbore.

For example, the computing device can output data corresponding to an isotopic data point generated by the computing device (e.g., in block 504), a depth associated with the isotopic data point (e.g., a depth determined by the computing device in block 506), a relationship between the isotopic data point and a depth associated with the isotopic data points (e.g., the relationship determined by the computing device in block 508), or any other data received by the computing device or generated by the computing device. The computing device can output the data in various forms, including, for example, as a chart, a plot, a graph, etc., for determining geological information about the wellbore. For example, FIG. 6 is an example of a graph 600 including isotopic data points that can be generated by a computing device.

Figure 6:
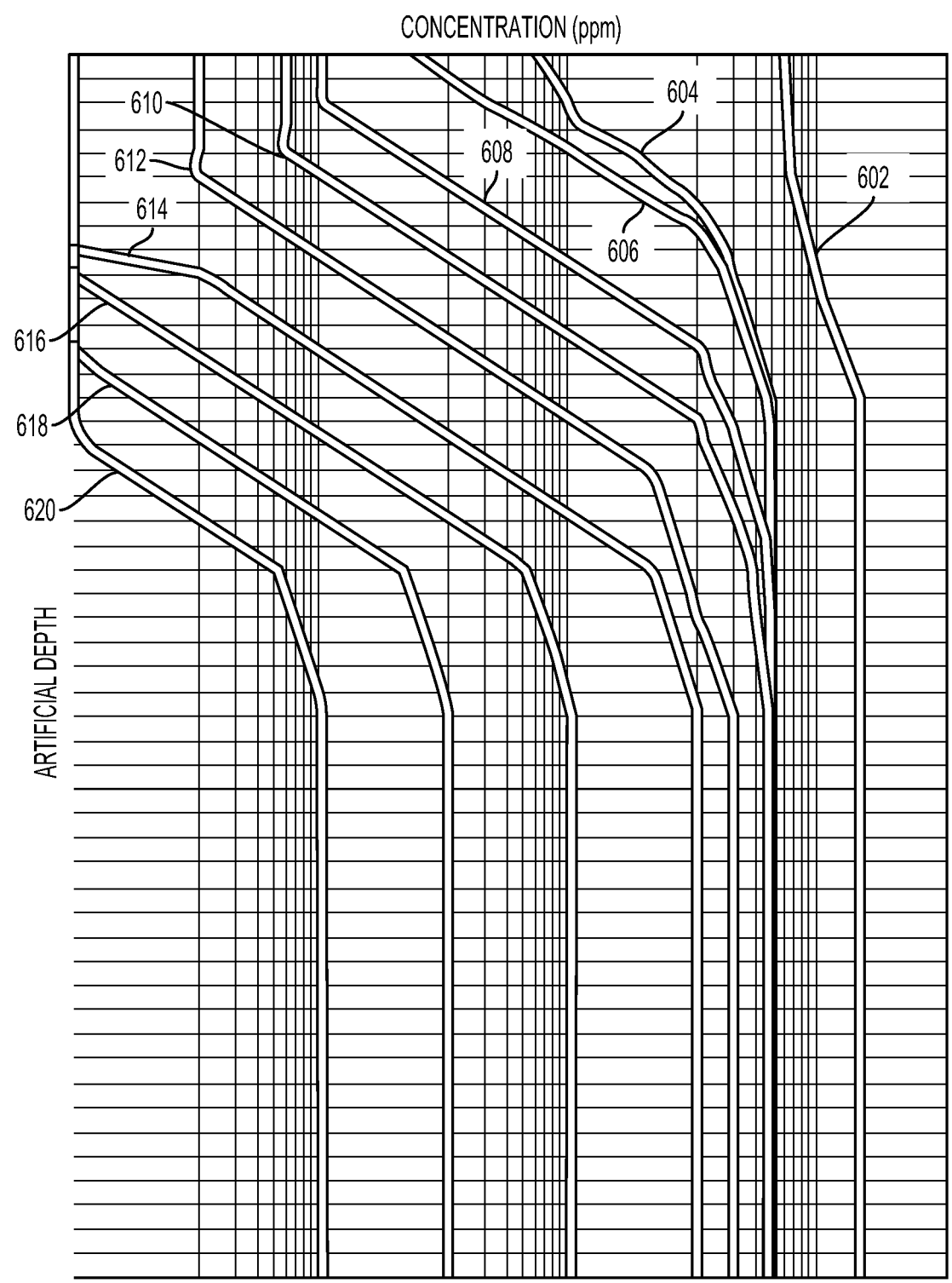
FIG. 6 is an example of a graph including isotopic data points that can be generated by a computing device according to one example of the present disclosure.

In the example depicted in FIG. 6, the graph 600 includes isotopic data points associated with various depths within a wellbore and an amount or concentration of a carbon isotope in a mud gas sample from a depth within the wellbore. For example, the line 602 includes various data points showing an amount (e.g., concentration level) of C1 in mud gas samples from various depths within the wellbore. The line 604 includes various data points showing a concentration level of C2 in mud gas samples from various depths within the wellbore. The line 606 includes various data points showing a concentration level of C3 in mud gas samples from various depths within the wellbore. The line 608 includes various data points showing a concentration level of C4 in mud gas samples from various depths within the wellbore. The line 610 includes various data points showing a concentration level of C5 in mud gas samples from various depths within the wellbore. The line 612 includes various points showing a concentration level of C6 in mud gas samples from various depths within the wellbore. The line 614 includes various data points showing a concentration level of C7 in mud gas samples from various depths within the wellbore. The line 616 includes various data points showing a concentration level of C8 in mud gas samples from various depths within the wellbore. The line 618 includes various data points showing a concentration level of C9 in mud gas samples from various depths within the wellbore. The line 620 includes various data points showing a concentration level of C10 in mud gas samples from various depths within the wellbore.

In some examples, an isotopic data point generated by the computing device can indicate a hydrocarbon composition of the mud gas sample associated with the isotopic data point. For example, the line 602 can include one or more data points that indicate an amount of methane in the mud gas samples from various depths within the wellbore. As another example, the line 604 can include one or more data points that indicate an amount of ethane in the mud gas samples from various depths within the wellbore.

In the example depicted in FIG. 6, the computing device can output the graph 600, which can be used to determine geological information about the wellbore.

Returning to FIG. 5, in some examples, in block 510, the computing device can generate and output data based at least in part on isotopic data received from the gas detector device as described above and generate and output a visual indicator associated with the data (e.g., generate and output a color coded chart, graph, plot, etc.). The visual indicator can be used to determine geological information about the wellbore.

In another example, in block 510, the computing device can determine geological information about the wellbore. For example, the computing device can determine geological information about the wellbore based at least in part on data received from a gas detector (e.g., data received in block 502). As an example, the computing device can determine a boundary of the wellbore based on the isotopic data points generated by the computing device (e.g., in block 504).

For example, the computing device can determine a relationship between the various isotopic data points and depths within the wellbore associated with the various isotopic data points by applying a regression analysis to the isotopic data points and depths within the wellbore associated with the various isotopic data (e.g., in block 508). In some examples, the relationship between the various isotopic data points and depths within the wellbore associated with the various isotopic data points can correspond to a best fitting line or other indicator of the relationship. The computing device can also execute one or more operations for determining a slope or inflection point of the relationship. For example, the computing device can determine the slope or inflection point by determining a first derivative or a second derivative of the best fitting line or the indicator of the relationship. In some examples, the computing device can then determine a boundary of the wellbore based at least in part on: i) the various isotopic data points; ii) the relationship between the various isotopic data points and depths within the wellbore associated with the various isotopic data points; or iii) the slope or inflection point of the relationship.

The computing device can determine the boundary of the wellbore as described above and also generate and output a visual indicator associated with the boundary (e.g., a color coded indicator corresponding to the boundary of the wellbore).

In this manner, a gas detector and a computing device can be used to determine geological information about a wellbore based on an amount of gas and a type of gas in a mud gas sample from the wellbore. In some examples, various mud gas samples from multiple wellbores can be used to determine geological information about the multiple wellbores. For example, multiple gas detectors can be used to analyze various mud gas samples from within the multiple wellbores to determine an amount and a type of gas in the various mud gas samples. Each gas detector can transmit isotopic data indicating an amount and a type of gas in each mud gas sample to one or more computing devices. Each computing device can generate one or more isotopic data points, determine geological information about the one or more of the wellbores, or output data for determining geological information about the one or more of the wellbores based on data received from the gas detectors in substantially the same manner as described above.

In some aspects, systems and methods for analyzing isotopes of a gas from a wellbore to determine geological information associated with the wellbore are provided according to one or more of the following examples:

Example #1: A method can include receiving, by a processing device and from a first gas-detecting device, isotopic data associated with a stream of a mud gas sample from a wellbore as the mud gas sample exits the wellbore. The isotopic data can indicate a type and an amount of a gas in the mud gas sample. The method can also include generating, by the processing device, a plurality of isotopic data points indicating a hydrocarbon composition of the mud gas sample based on the isotopic data. The method can also include determining, by the processing device, depths associated with the plurality of isotopic data points. The method can further include determining, by the processing device, a relationship between the plurality of isotopic data points and depths associated with the plurality of isotopic data points. The method can also include outputting, by the processing device, data indicating the plurality of isotopic data points, depths associated with the plurality of isotopic data points, and the relationship between the plurality of isotopic data points and the depths associated with the plurality of data points for determining geological information about the wellbore.

Example #2: The method of Example #1 may feature determining the relationship between the plurality of isotopic data points and depths associated with the plurality of isotopic data points including applying, by the processing device, a regression analysis to the plurality of isotopic data points and depths associated with the plurality of isotopic data points to determine the relationship.

Example #3: The method of any of Examples #1-2 may feature determining, by the processing device, a boundary of the wellbore based at least in part on the plurality of isotopic data points, the boundary indicating a shape of the wellbore.

Example #4: The method of Example #3 may feature determining the boundary of the wellbore including: determining, by the processing device, a slope or an inflection point of the relationship between the plurality of isotopic data points and depths associated with the plurality of isotopic data points; and determining the boundary based at least in part on the slope or the inflection point.

Example #5: The method of Example #4 may feature determining the slope or the inflection point of the relationship between the plurality of isotopic data points and depths associated with the plurality of isotopic data points including: determining, by the processing device, a first derivative of the relationship between the plurality of isotopic data points and depths associated with the plurality of isotopic data points; and determining, by the processing device, a second derivative of the relationship between the plurality of isotopic data points and depths associated with the plurality of isotopic data points.

Example #6: The method of any of Examples #1-5 may feature determining isotopic data associated with the stream of the mud gas sample using chromatography isotope-ratio mass spectrometry.

Example #7: The method of any of Examples #1-6 may feature determining the geological information about the wellbore including determining information about a seal, a barrier, a good communication zone, or gas diffusion within the wellbore.

Example #8: The method of any of Examples #1-7 may feature receiving, by the processing device, isotopic data indicating an amount and a type of a first gas in the mud gas sample from the first gas-detecting device. The first gas can include a first carbon isotope or a first hydrogen isotope. The method can also include receiving, by the processing device, isotopic data indicating an amount and a type of a second gas in the mud gas sample from the first gas-detecting device. The second gas can include a second carbon isotope or a second hydrogen isotope. The method can also include determining, by the processing device, a ratio between the amount of the first gas and the amount of the second gas by comparing the amount of the first gas and the amount of the second gas. The method can also include outputting, by the processing device, data indicating the ratio between the amount of the first gas and the amount of the second gas.

Example #9: The method of any of Examples #1-8 may feature: receiving, by the processing device and from a second gas-detecting device, isotopic data indicating an amount and a type of a first gas in a first mud gas sample entering the wellbore; receiving, by the processing device, isotopic data indicating an amount and a type of a second gas in a second mud gas sample exiting the wellbore from the first gas-detecting device; determining, by the processing device, a ratio between the amount of the first gas entering the wellbore and the amount of the second gas exiting the wellbore; and outputting, by the processing device, data indicating the ratio between the amount of the first gas and the amount of the second gas.

Example #10: The method of any of Examples #1-9 may feature: receiving, by the processing device, isotopic data associated with a plurality of streams of mud gas samples from a plurality of wellbores as each stream of mud gas sample exits a wellbore of the plurality of wellbores; generating, by the processing device, a plurality of isotopic data points indicating hydrocarbon compositions of each mud gas sample based on the isotopic data; determining, by the processing device, depths within the plurality of wellbores associated with the plurality of isotopic data points of each mud gas sample; determining, by the processing device, the relationship between the plurality of isotopic data points of each mud gas sample and depths associated with the plurality of isotopic data points of each mud gas sample; and outputting, by the processing device, data associated with a mud gas sample exiting each wellbore of the plurality of wellbores, the data corresponding to isotopic data points associated with the wellbore, depths associated with the isotopic data points, and the relationship between the isotopic data points and depths within the wellbore associated with the isotopic data points for determining geological information about the plurality of wellbores.

Example #11: A system can include a first gas-detecting device positionable proximate to a wellbore for detecting a gas in a mud gas sample from the wellbore at a surface of the wellbore as the mud gas sample exits the wellbore. The system can further include a processing module communicatively coupled to the first gas-detecting device to receive isotopic data from the first gas-detecting device and use the isotopic data to determine geological information about the wellbore. The isotopic data can represent an amount of gas and a type of gas detected by the first gas-detecting device.

Example #12: The system of Example #11 may feature the first gas-detecting device being positionable proximate to the wellbore to detect a type and an amount of a carbon isotope or a hydrogen isotope in the mud gas sample detected at the surface of the wellbore.

Example #13: The system of any of Examples #11-12 may feature the first gas-detecting device including at least one of a mass spectrometer or a cavity ring-down spectrometer.

Example #14: The system of any of Examples #11-13 may feature the first gas-detecting device being positionable proximate to the wellbore to detect a concentration level of a carbon isotope or a hydrogen isotope in the mud gas sample detected at the surface of the wellbore.

Example #15: The system of any of Examples #11-14 may feature a second gas-detecting device positionable proximate to the wellbore for detecting a gas in a fluid and gas mixture entering the wellbore. The system may also feature the processing module being communicatively coupled to the second gas-detecting device for receiving data indicating an amount of gas and a type of gas entering the wellbore from the second gas-detecting device.

Example #16: A non-transitory computer-readable storage medium having program code that is executable by a processor device to cause a computing device to perform operations. The operations can include receiving isotopic data associated with a stream of a mud gas sample from a first gas-detecting device as the mud gas sample exits a wellbore. The isotopic data can indicate an amount and a type of a gas in the mud gas sample. The operations can also include generating a plurality of isotopic data points indicating a hydrocarbon composition of the mud gas sample based on the isotopic data. The operations can also include determining depths associated with the plurality of isotopic data points. The operations can also include determining a relationship between the plurality of isotopic data points and depths associated with the plurality of isotopic data points. The operations can also include outputting data indicating the plurality of isotopic data points, depths associated with the plurality of isotopic data points, and the relationship between the plurality of isotopic data points and the depths associated with the plurality of data points for determining geological information about the wellbore.

Example #17: The storage medium of Example #16 may feature the operations of: receiving isotopic data indicating an amount and a type of a first gas in a first mud gas sample entering the wellbore from a second gas-detecting device; receiving isotopic data indicating an amount and a type of a second gas in a second mud gas exiting the wellbore from the first gas-detecting device; determining a ratio between the amount of the first gas and the amount of the second gas; and outputting data indicating the ratio between the amount of the first gas and the amount of the second gas.

Example #18: The storage medium of any of Examples #16-17 may feature the operation of determining a boundary of the wellbore based at least in part on the plurality of isotopic data points. The boundary can indicate a shape of the wellbore.

Example #19: The storage medium of Example #18 may feature the operation of determining the boundary of the wellbore including: determining a first derivative of the relationship between the plurality of isotopic data points and depths associated with the plurality of isotopic data points; determining a second derivative of the relationship between the plurality of isotopic data points and depths associated with the plurality of isotopic data points; determining a slope or an inflection point of the relationship between the plurality of isotopic data points and depths associated with the plurality of isotopic data points based at least in part on the first derivative or the second derivative; and determining the boundary based at least in part on the slope or the inflection point.

Example #20: The storage medium of any of Examples #16-19 may feature the operation of determining the relationship between the plurality of isotopic data points and depths associated with the plurality of isotopic data points including applying a regression analysis to the plurality of isotopic data points and the depths associated with the plurality of isotopic data points to determine the relationship.

The foregoing description of certain examples, including illustrated examples, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure.

What is claimed is:

1. A method comprising:
   detecting, by a first gas-detecting device, isotopic data associated with a stream of a mud gas sample from a wellbore, the isotopic data indicating a type and an amount of a gas in the mud gas sample;
   receiving, by a processing device, the isotopic data;
   generating, by the processing device, a plurality of isotopic data points indicating a hydrocarbon composition of the mud gas sample based on the isotopic data;
   determining, by the processing device, depths associated with the plurality of isotopic data points;
   determining, by the processing device, a relationship between the plurality of isotopic data points and depths associated with the plurality of isotopic data points by applying a regression analysis to the plurality of isotopic data points and depths associated with the plurality of isotopic data points to determine the relationship;
   determining, by the processing device, a boundary of the wellbore based at least in part on the plurality of isotopic data points, the boundary indicating a shape of the wellbore, wherein determining the boundary of the wellbore further comprises:
   determining, by the processing device, a slope or an inflection point of the relationship between the plurality of isotopic data points and depths associated with the plurality of isotopic data points; and
   determining the boundary based at least in part on the slope or the inflection point; and
   outputting, by the processing device, data indicating the plurality of isotopic data points, depths associated with the plurality of isotopic data points, the relationship between the plurality of isotopic data points and the depths associated with the plurality of isotopic data points, and the boundary of the wellbore for determining geological information about the wellbore.

2. The method of claim 1 wherein determining the slope or the inflection point of the relationship between the plurality of isotopic data points and depths associated with the plurality of isotopic data points includes:
   determining, by the processing device, a first derivative of the relationship between the plurality of isotopic data points and depths associated with the plurality of isotopic data points; and
   determining, by the processing device, a second derivative of the relationship between the plurality of isotopic data points and depths associated with the plurality of isotopic data points.

3. The method of claim 1, further comprising determining isotopic data associated with the stream of the mud gas sample using chromatography isotope-ratio mass spectrometry.

4. The method of claim 1, wherein determining the geological information about the wellbore includes determining information about a seal, a barrier, a good communication zone, or gas diffusion within the wellbore.

5. The method of claim 1, further comprising:
   receiving, by the processing device, isotopic data indicating an amount and a type of a first gas in the mud gas sample from the first gas-detecting device, the first gas including a first carbon isotope or a first hydrogen isotope;
   receiving, by the processing device, isotopic data indicating an amount and a type of a second gas in the mud gas sample from the first gas-detecting device, the second gas including a second carbon isotope or a second hydrogen isotope;
   determining, by the processing device, a ratio between the amount of the first gas and the amount of the second gas by comparing the amount of the first gas and the amount of the second gas; and
   outputting, by the processing device, data indicating the ratio between the amount of the first gas and the amount of the second gas.

6. The method of claim 1, further comprising:
   receiving, by the processing device and from a second gas-detecting device, isotopic data indicating an amount and a type of a first gas in a first mud gas sample entering the wellbore;
   receiving, by the processing device, isotopic data indicating an amount and a type of a second gas in a second mud gas sample exiting the wellbore from the first gas-detecting device;
   determining, by the processing device, a ratio between the amount of the first gas entering the wellbore and the amount of the second gas exiting the wellbore; and
   outputting, by the processing device, data indicating the ratio between the amount of the first gas and the amount of the second gas.

7. The method of claim 1, further comprising:
   receiving, by the processing device, isotopic data associated with a plurality of streams of mud gas samples from a plurality of wellbores as each stream of mud gas sample exits a wellbore of the plurality of wellbores;

generating, by the processing device, a plurality of isotopic data points indicating hydrocarbon compositions of each mud gas sample based on the isotopic data;

determining, by the processing device, depths within the plurality of wellbores associated with the plurality of isotopic data points of each mud gas sample;

determining, by the processing device, the relationship between the plurality of isotopic data points of each mud gas sample and depths associated with the plurality of isotopic data points of each mud gas sample; and outputting, by the processing device, data associated with a mud gas sample exiting each wellbore of the plurality of wellbores, the data corresponding to isotopic data points associated with the wellbore, depths associated with the isotopic data points, and the relationship between the isotopic data points and depths within the wellbore associated with the isotopic data points for determining geological information about the plurality of wellbores.

8. The method of claim 1, further comprising:
Generating, by the processing device, a visual indicator associated with the boundary of the wellbore.

9. The method of claim 8, further comprising:
Outputting, by the processing device, the visual indicator associated with the boundary.

10. The method of claim 8, wherein the visual indicator is a color coded indicator corresponding to the boundary of the wellbore.

11. A system comprising:
a first gas-detecting device positionable proximate to a wellbore for detecting a gas in a mud gas sample from the wellbore at a surface of the wellbore as the mud gas sample exits the wellbore; and a processing module communicatively coupled to the first gas-detecting device to receive isotopic data from the first gas-detecting device and use the isotopic data to:
  determine, by the processing module, depths associated with the isotopic data;
  determine, by the processing module, a relationship between the isotopic data and depths associated with the isotopic data by applying a regression analysis to the isotopic data and depths associated with the isotopic data to determine the relationship;
  determine, by the processing module, a boundary of the wellbore based at least in part on the isotopic data, the boundary indicating a shape of the wellbore, wherein determining the boundary of the wellbore further comprises:
    determine, by the processing module, a slope or an inflection point of the relationship between the isotopic data and depths associated with the isotopic data; and
    determine the boundary based at least in part on the slope or the inflection point; and
  determine, by the processing module, geological information about the wellbore using the isotopic data, depths associated with the isotopic data, the relationship between the isotopic data and the depths associated with the isotopic data, and the boundary of the wellbore, the isotopic data representing an amount of gas and a type of gas detected by the first gas-detecting device.

12. The system of claim 11, wherein the first gas-detecting device is positionable proximate to the wellbore to detect a type and an amount of a carbon isotope or a hydrogen isotope in the mud gas sample detected at the surface of the wellbore.

13. The system of claim 11, wherein the first gas-detecting device includes at least one of a mass spectrometer or a cavity ring-down spectrometer.

14. The system of claim 11, wherein the first gas-detecting device is positionable proximate to the wellbore to detect a concentration level of a carbon isotope or a hydrogen isotope in the mud gas sample detected at the surface of the wellbore.

15. The system of claim 11, further comprising:
a second gas-detecting device positionable proximate to the wellbore for detecting a gas in a fluid and gas mixture entering the wellbore and wherein the processing module is communicatively coupled to the second gas-detecting device for receiving data indicating an amount of gas and a type of gas entering the wellbore from the second gas-detecting device.

16. A non-transitory computer-readable storage medium having program code that is executable by a processor device to cause a computing device to perform operations, the operations comprising:
receiving isotopic data associated with a stream of a mud gas sample from a first gas-detecting device as the mud gas sample exits a wellbore, the isotopic data indicating an amount and a type of a gas in the mud gas sample;

generating a plurality of isotopic data points indicating a hydrocarbon composition of the mud gas sample based on the isotopic data;

determining depths associated with the plurality of isotopic data points;

determining a relationship between the plurality of isotopic data points and depths associated with the plurality of isotopic data points by applying a regression analysis to the plurality of isotopic data points and depths associated with the plurality of isotopic data points to determine the relationship;

determining a boundary of the wellbore based at least in part on the plurality of isotopic data points, the boundary indicating a shape of the wellbore, wherein determining the boundary of the wellbore further comprises:
  determining a slope or an inflection point of the relationship between the plurality of isotopic data points and depths associated with the plurality of isotopic data points; and
  determining the boundary based at least in part on the slope or the inflection point; and outputting data indicating the plurality of isotopic data points, depths associated with the plurality of isotopic data points, the relationship between the plurality of isotopic data points and the depths associated with the plurality of isotopic data points, and the boundary of the wellbore for determining geological information about the wellbore.

17. The non-transitory computer-readable storage medium of claim 16, further comprising program code to cause the computing device to perform the operation of:
receiving isotopic data indicating an amount and a type of a first gas in a first mud gas sample entering the wellbore from a second gas-detecting device;

receiving isotopic data indicating an amount and a type of a second gas in a second mud gas exiting the wellbore from the first gas-detecting device;

determining a ratio between the amount of the first gas and the amount of the second gas; and outputting data indicating the ratio between the amount of the first gas and the amount of the second gas.

18. The non-transitory computer-readable storage medium of claim 16, wherein the operation of determining the boundary of the wellbore includes:
    determining a first derivative of the relationship between the plurality of isotopic data points and depths associated with the plurality of isotopic data points; and
    determining a second derivative of the relationship between the plurality of isotopic data points and depths associated with the plurality of isotopic data points.

\* \* \* \* \*